United States Patent [19]
Morizumi

[11] Patent Number: 6,142,932
[45] Date of Patent: Nov. 7, 2000

[54] FRONT END STRUCTURE OF STEREOSCOPIC ENDOSCOPE INCLUDING AN ELONGATED LENS

[75] Inventor: Masaaki Morizumi, Omiya, Japan

[73] Assignee: Fuji Photo Optical Co., Ltd., Saitama, Japan

[21] Appl. No.: 09/317,896

[22] Filed: May 25, 1999

[30] Foreign Application Priority Data

Jun. 19, 1998 [JP] Japan .................................. 10-172926

[51] Int. Cl.[7] .............................. A61B 1/06; H04N 13/02
[52] U.S. Cl. ........................ 600/166; 600/111; 600/176; 348/47; 348/75; 359/725
[58] Field of Search ................................... 600/106, 111, 600/112, 166, 176, 177, 920; 348/45, 46, 47, 48, 49, 75; 359/462, 827, 377, 376, 725

[56] References Cited

U.S. PATENT DOCUMENTS 5,702,350 12/1997 Vry et al. ................................. 600/166
5,989,185 11/1999 Miyazaki ................................. 600/166

FOREIGN PATENT DOCUMENTS 06331939 12/1994 Japan .............................. G02B 27/22

*Primary Examiner*—Jon Henry
*Attorney, Agent, or Firm*—Snider & Associates; Ronald R. Snider

[57] ABSTRACT

A front end lens 11 of a pair of objective lenses 32R, 32L disposed the object-side end face of a front end part 1 of a stereoscopic endoscope has a so-called D-cut lens form in which both side portions of a spherical lens are cut off, whereby spaces for arranging illumination windows 13, lens surface washing nozzles 15, and heads of fastening screws 14 for fastening the front end part 1 to a front end part main body 2 are secured at the front end face of the front end part 1, while keeping its function of yielding a sufficient angle of convergence θ. A positioning pin 16 formed in the front end part main body 2 is inserted into a pin insertion groove 17 formed in a protrusion 12 of the front end part 1 at an eccentric position of the protrusion 12, whereby both members 1, 2 are inhibited from rotating relative to each other, and the relative positional relationship between the front end lens 11 and the pair of objective optical systems 32R, 32L can reliably be fixed.

5 Claims, 5 Drawing Sheets

OBJECT SIDE ← → IMAGE SIDE

FRONT END STRUCTURE OF STEREOSCOPIC ENDOSCOPE INCLUDING AN ELONGATED LENS

RELATED APPLICATIONS

This application claims the priority of Japanese Patent Application No. 10-172926 filed on Jun. 19, 1998, which is incorporated herein by reference.

BACKGROUND OF THE INVENTION

1. Field of the Invention

The present invention relates to a stereoscopic endoscope by which a part to be inspected such as the inside of a body cavity is stereoscopically observed by means of a pair of objective optical systems disposed at the front end of its inserting portion; and, more specifically, to a structure of the front end part of the inserting portion thereof.

2. Description of the Prior Art

Recently, surgical techniques in which endoscopes are used for observing parts to be inspected within body cavities and performing operations on diseased parts within the body cavities have been prevailing. For making diagnoses more accurately and alleviating the suffering of patients, the endoscopes have been technically improved. In particular, for performing a diagnosis more accurately within a body cavity, it is useful to obtain depth information within the body cavity. Stereoscopic endoscopes have been known to respond to such a demand.

In a stereoscopic endoscope, for the sake of workability, a pair of objective optical systems corresponding to the right and left eyes are assembled therein with their optical axes being parallel to each other. When such parallelism is secured in their optical axes, it is necessary that the base length formed by the optical axes of the pair of objective optical systems be remarkably shortened in view of easiness in viewing.

In practice, however, it has been difficult to extremely shorten the base length due to mechanical restrictions. As a consequence, easily viewable three-dimensional images have been hard to obtain.

In order to overcome such a problem, the assignee has already proposed a stereoscopic endoscope in which a convex front end lens is disposed on the object side of a pair of objective optical systems, so that an easily viewable three-dimensional image can be obtained even when the base length formed by the optical axes of the pair of optical systems is not set short (Japanese Unexamined Patent Publication No. 6-331939).

In such a stereoscopic endoscope, however, the front end lens is disposed at the front end face of the front end part of the endoscope and thereby occupies the major space of the front end face.

In general, the front end face of the front end part of an endoscope is formed with an air/water discharge hole, through which air or washing water is discharged. A space for arranging the air/water discharge hole is necessary in the front end face of the front end part in the above-mentioned stereoscopic endoscope having the front end lens as well.

When the head of a screw for securing the front end part to a front end part main body is to be positioned at the front end face of the front end part, a space therefor is also needed.

Further, an illumination optical system for illuminating an object to be viewed is disposed at the front end part of such an endoscope. As shown in FIG. 9, when a front end lens 111 is disposed on the object side of an illumination optical system 113, light beams 120, of the light from the illumination optical system 113, reflected by the object-side face of the front end lens 111 enter the inside of an objective optical system 130 from its front end face, thereby generating noise light with respect to the original subject image light and deteriorating the image quality. Therefore, it is desirable that the front end part of such an illumination optical system 113 be positioned on the front end face of the front end part of the endoscope.

SUMMARY OF THE INVENTION

In view of such circumstances, it is an object of the present invention to provide a front end structure of a stereoscopic endoscope which can secure spaces for arranging an air/water discharge hole, the front end part of an illumination optical system, and other desirable members, while being able to yield an easily viewable image without the base length of a pair of objective optical systems in the stereoscopic endoscope being set short.

The present invention provides a front end structure of a stereoscopic endoscope in which a pair of objective optical systems are disposed at a front end of an inserting portion, the front end structure comprising:

a pair of lens barrel portions for holding and accommodating the pair of objective optical systems, respectively;

a lens barrel main body for supporting the pair of lens barrel portions such that the lens barrel portions project toward an object;

a front end part main body formed with a pair of insertion holes adapted to receive the pair of lens barrel portions, respectively; and a cap-like front end part adapted to mate with an object-side end part of the front end part main body;

wherein a lens for guiding a pair of subject image light beams for right and left eyes to the pair of objective optical systems is disposed at an object-side end face of the front end part, the lens having a form elongated in a direction along which the pair of objective optical systems align with each other in a state where the front end part and the front end part main body mate with each other.

Preferably, each mating portion between the front end part main body and the front end part has a tubular or cylindrical form, and, in a state where the front end part main body and the front end part mate with each other, a positioning pin disposed at an eccentric position of one member thereof is inserted into a pin insertion groove formed in the other member, so that the two members are prevented from rotating with respect to each other.

The cap-like front end may be provided with a lens surface washing nozzle and an illumination window, in addition to the lens.

The cap-like front end may be provided with a head of a fastening screw for connecting the front end part to the front end part main body, in addition to the lens.

The fastening screw for connecting the front end part to the front end part main body may be inserted between the front end part main body and a mating side portion of the front end part.

DESCRIPTION OF THE PREFERRED EMBODIMENTS

In the following, embodiments of the present invention will be explained with reference to the accompanying drawings.

The front end structure of the stereoscopic endoscope in accordance with these embodiments is employed in a so-called electronic endoscope apparatus in which a front end part of the inserting portion of the endoscope has a solid-state imaging device (CCD).

Namely, in this electronic endoscope apparatus, a luminous flux carrying subject information incident on an objective optical system from the front end side of the elongated inserting portion adapted to be inserted into a body cavity or the like is focused onto a CCD, the video signal data captured by the CCD is transmitted to a control unit connected to an operating section and is subjected to signal processing in the control unit, and then the subject image is displayed on a monitor.

On the monitor, right- and left-eye images having a parallax with respect to each other are displayed alternately. By viewing these color images through a pair of shutter glasses, a viewer can see the subject image three-dimensionally. The inserting portion is provided with an illumination light transmitting means for supplying illumination light from a light source apparatus, and an illumination optical system for emitting thus transmitted light through an illumination window so as to illuminate the subject.

Figure 1:
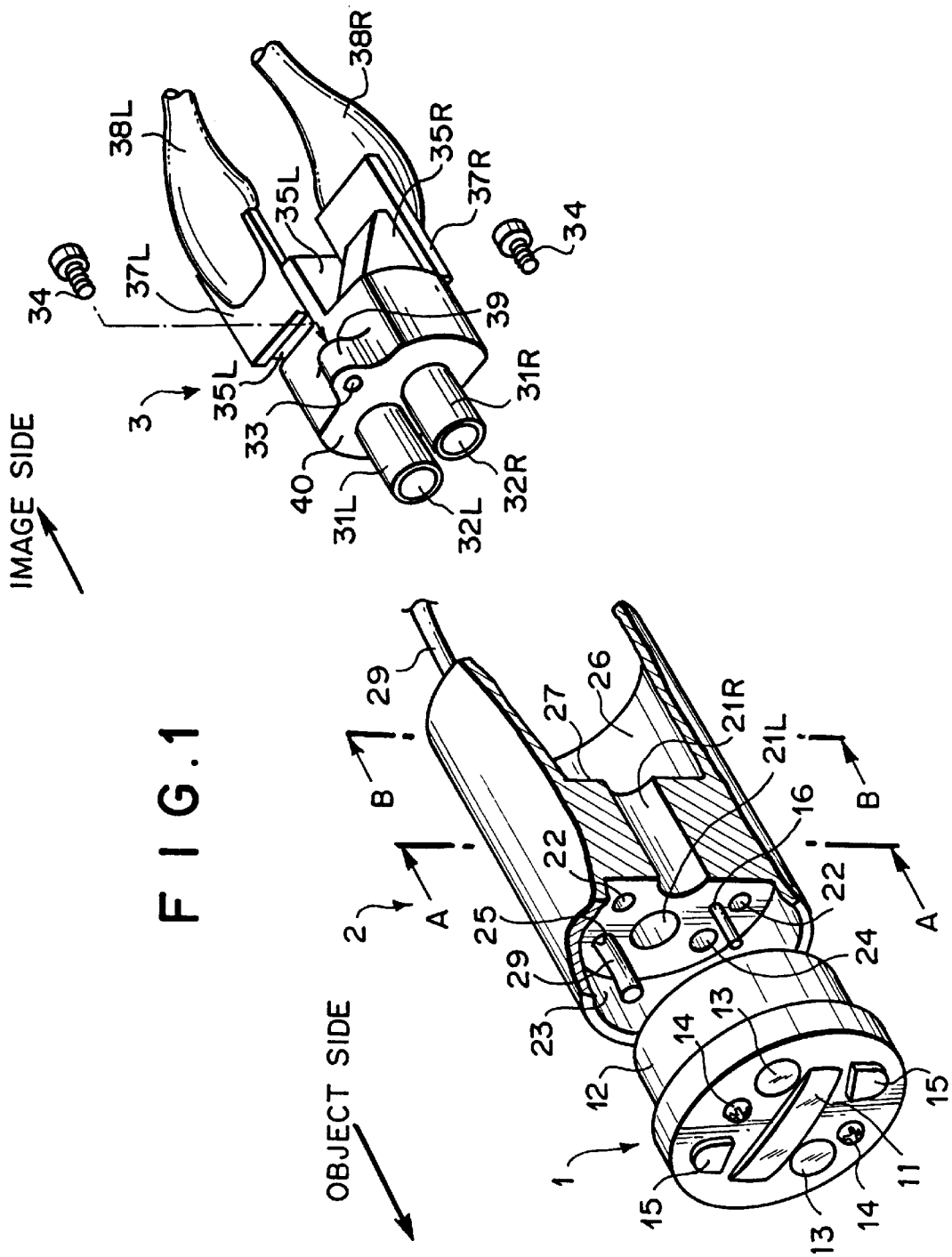
FIG. 1 is a perspective view showing the front end structure of the stereoscopic endoscope in accordance with an embodiment of the present invention.

FIG. 1 is a view showing the front end structure of the stereoscopic endoscope in accordance with an embodiment of the present invention.

The front end portion of this stereoscopic endoscope comprises, successively from the object side, a front end part 1, a front end part main body 2, and a lens barrel main body 3.

Figure 8:
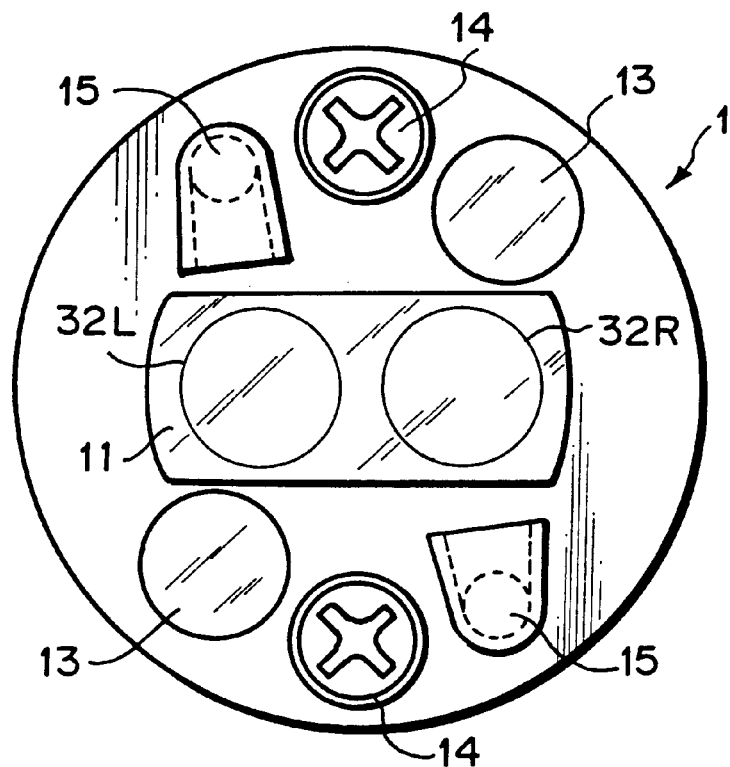
FIG. 8 is a front view showing the front end face of the front end part shown in FIG. 1.
Figure 9:
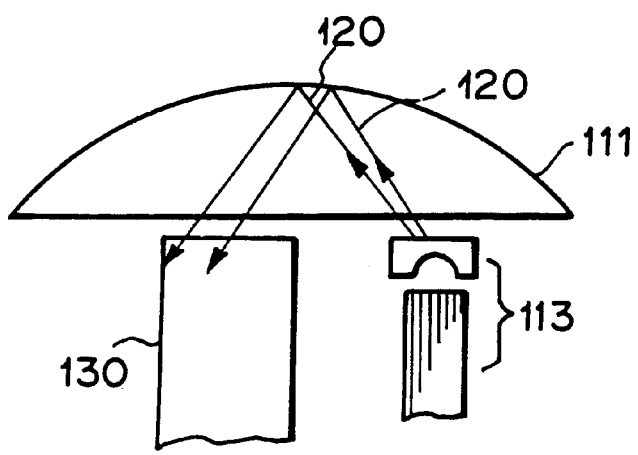
FIG. 9 is a section view showing a conventional example.

The front end part 1 is used as being assembled to the object side of the front end part main body 2. As shown in FIG. 8, the front end face of the front end part 1 is provided with a D-cut, elongated front end lens 11 having a positive refracting power; whereas an illumination window 13, a lens surface washing nozzle 15, and a head of a fastening screw 14 for securing the front end part 1 to the front end part main body 2 are located in each of two spaces obtained by D-cutting the front end lens 11.

A protrusion 12 of the front end part 1 and a depression 23 of the front end part main body 2 mate with each other in a spigot/socket connection. At the positions where not-illustrated tapped holes formed at two locations on the upper and lower sides of the front end part 1 in parallel with the optical axis and tapped holes 22 formed at two locations on the upper and lower sides of the front end part main body 2 in parallel with the optical axis meet, these tapped holes are engaged with the fastening screws 14, whereby the front end part 1 and the front end part main body 2 are secured to each other.

The front end part main body 2 comprises a pair of lens barrel part insertion holes 21R, 21L formed parallel to each other; holes 24 for the illumination light transmitting means; tapped holes (not illustrated) for securing the lens barrel main body 3 assembled to the image side of the front end main body 2; and air/water supply channels 25, each containing a flexible tube 29 inserted therein, for supplying air and water to the lens surface washing nozzles 15 of the front end part 1. The flexible tube 29 is attached to the tubular end portion of its corresponding lens surface washing nozzle 15 projecting from the front end part 1 toward the front end part main body 2. The image-side end portion of the front end part main body 2 is formed with a cylindrical portion 26 extending toward the image side.

The lens barrel main body 3 comprises two tapped holes 33 formed in upper and lower flanges 39, respectively, for securing the front end part main body 2; a pair of lens barrel portions 31R, 31L, formed so as to project from a front wall face 40 of the lens barrel main body 3 including the front faces of the flanges 39 toward the front end part main body 2, for holding and accommodating a pair of objective optical systems 32R, 32L, respectively; a pair of circuit boards 37R, 37L mounting a pair of CCDs 36R, 36L (see FIG. 3), respectively; and a pair of rectangular prisms 35R, 35L for deflecting luminous fluxes from the objective optical systems 32R, 32L so as to make them incident on the CCDs 36R, 36L, respectively. The incident luminous fluxes carrying subject information from the object side are focused onto the imaging surfaces of the CCDs 36R, 36L, subjected to photoelectric conversion, and then transmitted as image data to a not-illustrated control unit by way of a pair of cables 38R, 38L drawn from the circuit boards 37R, 37L, respectively.

Figure 2:
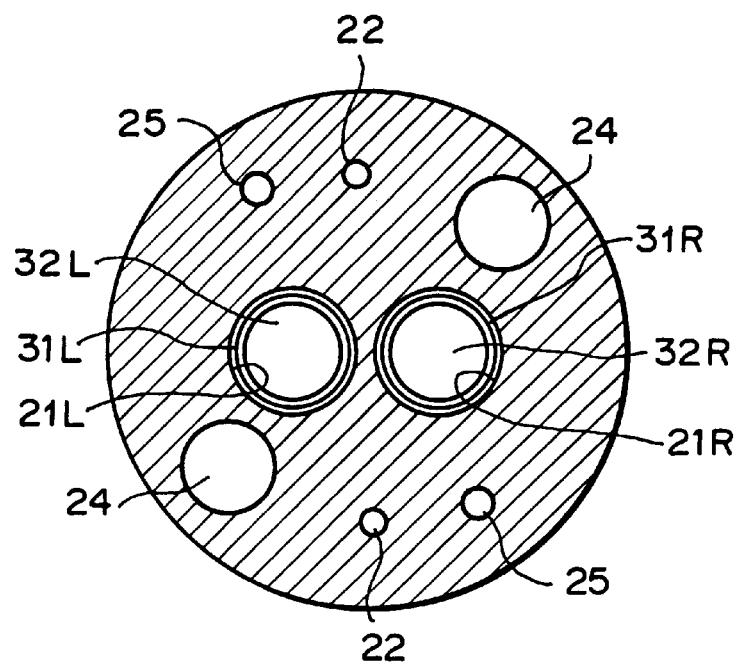
FIG. 2 is a sectional view taken along the line A—A of FIG. 1.

FIG. 2 shows a sectional view taken along the line A—A of FIG. 1. The front end part main body 2 and the lens barrel main body 3 are assembled to each other such that the lens barrel part insertion holes 21R, 21L are combined with their corresponding lens barrel portions 31R, 31L, each with a play. After being thus assembled to each other in a predetermined state, the front end part main body 2 and the lens barrel main body 3 are secured to each other as the tapped holes 33 of the flanges 39 formed at the upper and lower locations and the tapped holes (not illustrated) formed in the front end part main body 2 are engaged with fastening screws 34. Thus, the lens barrel main body 3 is inserted into the front end part main body 2 such that the front wall face 40 of the former and the bottom wall face 27 of the cylindrical portion 26 of the latter abut to each other, and they are screwed and secured to each other. Such securing enhances the screwing strength of the fastening screws 34, so that their holding states become favorable, and the axial positioning becomes easier, while dislocation is hard to occur.

Figure 5:
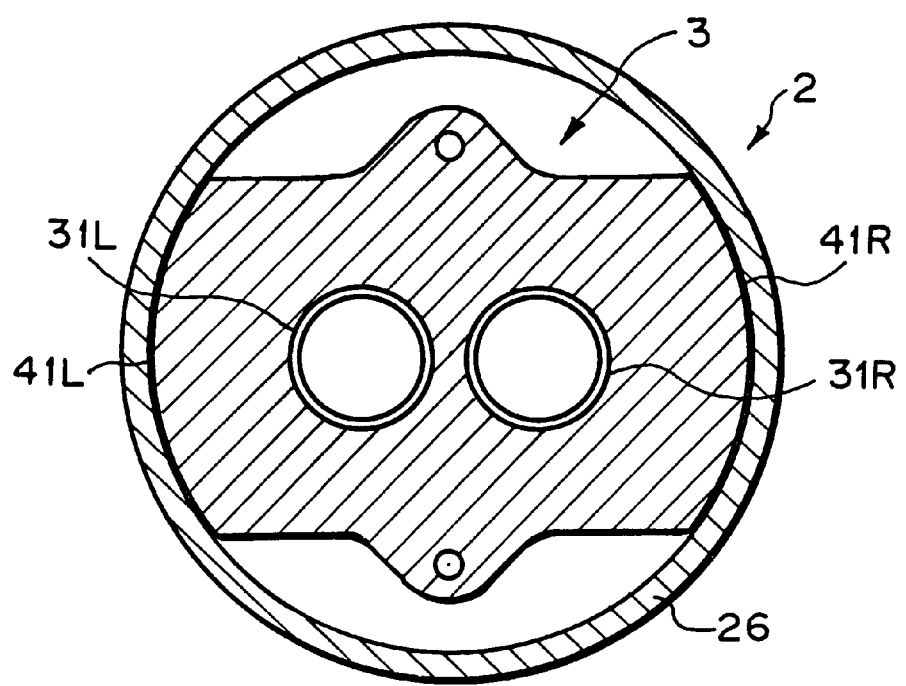
FIG. 5 is a sectional view taken along the line B—B of FIG. 1.

FIG. 5 shows a sectional view taken along the line B—B of FIG. 1. In the outer peripheral surface of the lens barrel main body 3, its right and left side portions 41R, 41L are formed as a part of a cylindrical surface having an outside diameter substantially the same as the inside diameter of the cylindrical portion 26 of the front end part main body 2, whereby the lens barrel main body 3 is allowed to slidably mate with the front end part main body 2. The axial length of the cylindrical portion 26 is set longer than the lens barrel portion 31R, 31L.

In the following, the configuration of optical system in accordance with this embodiment will be explained.

Figure 3:
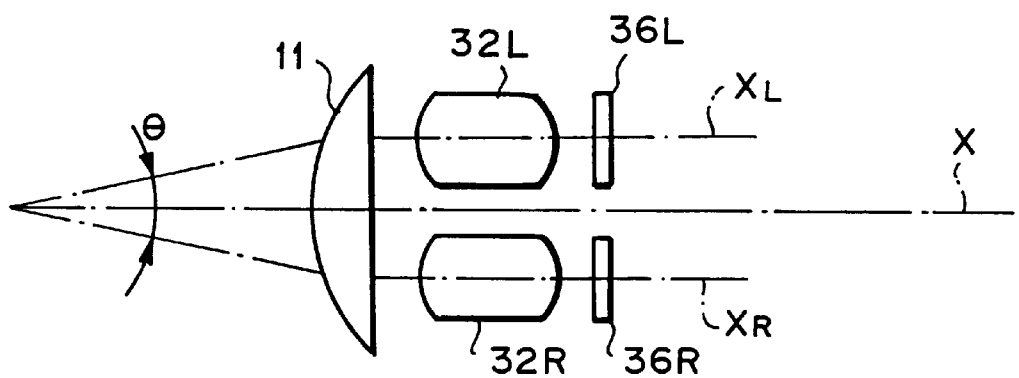
FIG. 3 is a conceptual view of an optical system in the embodiment shown in FIG. 1.

In the optical system used in the front end structure of the stereoscopic endoscope in accordance with this embodiment, the respective optical axes of the pair of objective optical systems 32R, 32L are parallel to each other as shown in FIG. 3.

In general, when images for right and left eyes obtained by a pair of objective optical systems form an angle therebetween approximating the angle of convergence upon viewing by both eyes of a viewer, their three-dimensional feel becomes favorable, and the viewer feels less fatigue. However, if a configuration in which the optical axes of the objective optical systems have an angle of convergence with respect to each other is employed for the sake of easiness in viewing, the working process will be complicated, and errors upon assembly and adjustment will increase.

Therefore, it is desirable to construct, as in this embodiment, for example, an optical system in which the front end lens 11 is disposed on the object side of the objective optical systems 32R, 32L such that an angle of convergence θ can be obtained for right and left eyes while the respective optical axes of the objective optical systems 32R, 32L are parallel to each other. Here, the front end lens 11 is a lens having a focal length corresponding to the distance to the subject, and a positive refracting power; whereas the objective optical systems 32R, 32L are combined to each other so as to form an image at infinity. When the optical axes are disposed parallel to each other, the assembling step can easily be configured as a unit, errors in assembly and adjustment can be reduced, and the cost can be cut down.

In the case of the front end structure of the stereoscopic endoscope in which the front end lens 11 is thus disposed, the front end part 1 and the front end part main body 2 mate with each other in a spigot/socket connection, whereas the front end part main body 2 and the lens barrel main body 3 slidably mate with each other. Consequently, as compared with a conventional front end structure (in which the lens barrel main body is simply accommodated within the cylindrical portion of the front end part main body), assembling can be carried out in a state where a high accuracy and numerical control are attained in the optical-axis alignment of the front end lens 11, the objective optical systems 32R, 32L, and the CCDs 36R, 36L, or the like.

Also, since the axial length of the cylindrical portion 26 is set longer than the lens barrel portion 31R, 31L of the lens barrel main body 3, the front end part main body 2 can perform a guiding function when the lens barrel portions 31R, 31L are inserted into their corresponding lens barrel insertion holes 21R, 21L as the front end part main body 2 and the lens barrel main body 3 slidably mate with each other.

While the above-mentioned embodiment is configured such that the front end lens 11 is positioned at the front end face of the front end part 1, this front end face is also provided with a pair of lens surface washing nozzles 15 and a pair of illumination windows 13 in addition to the front end lens 11. Further, the heads of the fastening screws 14 for connecting the front end part 1 to the front end part main body 2 are positioned at the front end face. Since spaces for arranging various kinds of members are thus necessary in the front end face of the front end part 1, it is desirable that the space for placing the front end lens 11 be reduced as much as possible.

When the front end lens 11 is a lens having a small diameter, however, it is hard to secure a length corresponding to the base length of the optical axes of the two objective lenses 32R, 32L.

Figure 4:
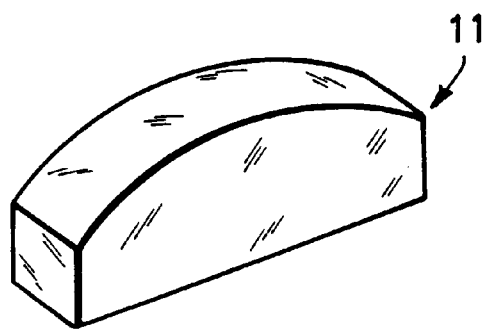
FIG. 4 is a perpective view showing the overall form of the front end lens shown in FIG. 1.

Therefore, in this embodiment, the front end lens 11 has a so-called D-cut lens form as shown in FIG. 4, in which both side portions of a spherical lens are cut off. When the front end lens 11 has a D-cut lens form, spaces for arranging various kinds of members can be secured in the front end face of the front end part 1, while keeping its function of yielding a sufficient angle of convergence θ.

Here, the front end lens 11 is formed such that its longitudinal direction coincides with a direction along which the objective optical systems 32R, 32L align with each other when the front end part 1 is secured to the front end part main body 2 by means of the fastening screws 14.

Figure 7:
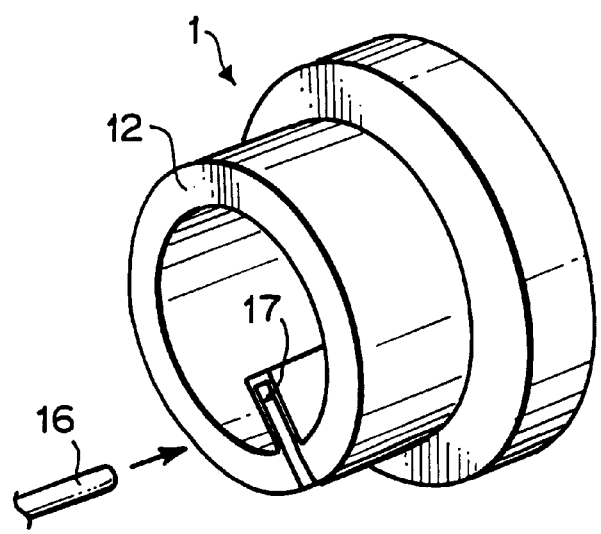
FIG. 7 is a view for explaining a structure for inhibiting the front end part and front end part main body shown in FIG. 1 from rotating relative to each other.

Also, as shown in FIG. 7, when the front end part 1 and the front end part main body 2 are mated with each other, a positioning pin 16 formed in the front end part main body 2 is inserted into a pin insertion groove 17 formed in the protrusion 12 of the front end part 1 at an eccentric position of the protrusion 12. As a consequence, these members 1, 2 are inhibited from rotating relative to each other, and the relative positional relationship between the front end lens 11 and the pair of objective optical systems 32R, 32L is reliably fixed.

The member for inhibiting the front end part 1 and the front end part main body 2 from rotating relative to each other is not restricted to that of the abovementioned embodiment. It may have any form as long as it can constitute a mechanism adapted to inhibit the members 1, 2 from moving in their rotational directions when they are mated with each other. though the fastening screws 14 are inserted into the tapped holes in the front end face of the front end part 1 toward the front end part main body 2 in this embodiment, fastening screws may be inserted between the front end part main body 2 and a mating side portion of the front end part 1, so as to screw these members 1, 2 to each other.

Figure 6:
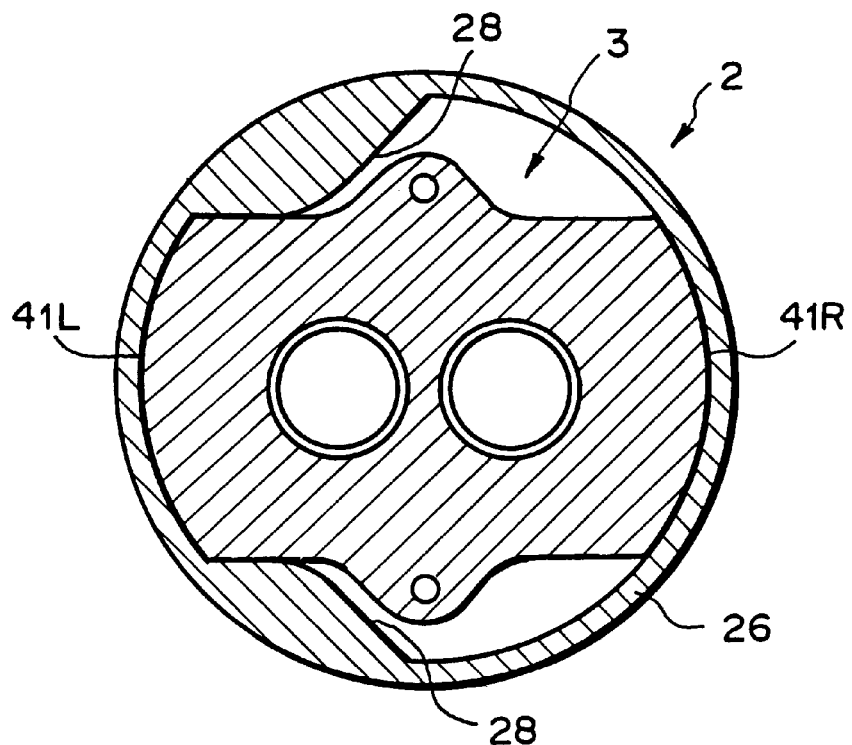
FIG. 6 is a sectional view showing a modified example of the embodiment shown in FIG. 1.

FIG. 6 is a schematic view showing a modified example of this embodiment.

In this modified example, a pair of rotation preventing protrusions 28 are formed on the upper and lower sides of the left-side outer peripheral surface portion 41L of the lens barrel main body 3 in the inner peripheral surface of the cylindrical portion 26 of the front end part main body 2. The pair of rotation preventing protrusions 28 hold the left-side outer peripheral portion 41L from upper and lower sides thereof, thereby preventing the lens barrel main body 3 from rotating with respect to the front end part main body 2.

As explained in the foregoing, in the front end structure of the stereoscopic endoscope in accordance with the present invention, the front end lens of a pair of objective optical systems disposed at the object-side end face of the front end part has a D-cut form, whereby large spaces can be secured in the widthwise direction of the elongated front end lens in the end face. As a consequence, air/water discharge holes, the front end part of an illumination optical system, heads of screws for securing the front end part, and the like can be arranged in thus secured spaces, while enabling easy assembly and allowing the angle of convergence to be set to a predetermined degree.

Thus, while an easily viewable image can be obtained, air and washing water can be discharged from the front end face of the front end part without difficulty, and the light reflected from the front end lens can be inhibited from entering the objective optical system as noise light.

What is claimed is:

1. A front end structure of a stereoscopic endoscope in which a pair of objective optical systems are disposed at a front end of an inserting portion, said front end structure comprising:

a pair of lens barrel portions for holding and accommodating said pair of objective optical systems, respectively;

a lens barrel main body for supporting said pair of lens barrel portions such that said lens barrel portions project toward an object;

a front end part main body formed with a pair of insertion holes adapted to receive said pair of lens barrel portions, respectively; and a cap-like front end part adapted to mate with an object-side end part of said front end part main body;

wherein a lens for guiding a pair of subject image light beams for right and left eyes to said pair of objective optical systems is disposed at an object-side end face of said front end part, said lens having a form elongated in a direction along which said pair of objective optical systems align with each other in a state where said front end part and said front end part main body mate with each other.

2. A front end structure of a stereoscopic endoscope according to claim 1, wherein each mating portion between said front end part main body and said front end part has a tubular or cylindrical form; and wherein, in a state where said front end part main body and said front end part mate with each other, a positioning pin disposed at an eccentric position of one member thereof is inserted into a pin insertion groove formed in the other member, so that the two members are prevented from rotating with respect to each other.

3. A front end structure of a stereoscopic endoscope according to claim 1, wherein said cap-like front end is provided with a lens surface washing nozzle and an illumination window, in addition to said lens.

4. A front end structure of a stereoscopic endoscope according to claim 1, wherein said cap-like front end is provided with a head of a fastening screw for connecting said front end part to said front end part main body, in addition to said lens.

5. A front end structure of a stereoscopic endoscope according to claim 1, wherein a fastening screw for connecting said front end part to said front end part main body is inserted between said front end part main body and a mating side portion of said front end part.

* * * * *